(12) United States Patent
Dal Farra et al.

(10) Patent No.: US 8,569,243 B2
(45) Date of Patent: Oct. 29, 2013

(54) SIRTUIN 6 ACTIVATING PEPTIDES AND COSMETIC OR PHARMACEUTICAL COMPOSITION CONTAINING THEM

(75) Inventors: Claude Dal Farra, Kerhonkson, NY (US); Nouha Domloge, Valbonne (FR); Jean-Marie Botto, Valbonne (FR); Isabelle Imbert, Cannes (FR); Nadine Pernodet, Huntington Station, NY (US)

(73) Assignees: ISP Investments Inc., Wilmington, DE (US); ELC Management LLC, Melville, NY (US)

( * ) Notice: Subject to any disclaimer, the term of this patent is extended or adjusted under 35 U.S.C. 154(b) by 0 days.

(21) Appl. No.: 13/166,836

(22) Filed: Jun. 23, 2011

(65) Prior Publication Data
US 2011/0318284 A1 Dec. 29, 2011

(30) Foreign Application Priority Data
Jun. 29, 2010 (FR) .................... 10 02698

(51) Int. Cl.
*A61K 38/08* (2006.01)
*A61Q 19/08* (2006.01)
*A61Q 17/04* (2006.01)
*C07K 7/06* (2006.01)

(52) U.S. Cl.
USPC ........ 514/18.8; 514/18.6; 514/21.7; 530/328; 530/329

(58) Field of Classification Search
None
See application file for complete search history.

(56) References Cited

U.S. PATENT DOCUMENTS

| | | | | |
|---|---|---|---|---|
| 5,516,507 A | * | 5/1996 | N'Guyen et al. | 424/59 |
| 2003/0166057 A1 | * | 9/2003 | Hildebrand et al. | 435/69.1 |

FOREIGN PATENT DOCUMENTS

| | | | |
|---|---|---|---|
| EP | 1955715 | 8/2008 | |
| EP | 1868631 | 7/2010 | |
| FR | 2883751 | 10/2006 | |
| FR | 2883752 | 10/2006 | |
| FR | 2883753 | 10/2006 | |
| FR | 2883754 | 10/2006 | |
| WO | WO90/12879 A2 * | 11/1990 | C12N 15/81 |
| WO | WO 2005066337 A2 * | 7/2005 | C12N 9/18 |
| WO | WO 2007104062 A2 * | 9/2007 | C40B 40/02 |

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-497.*
Bradley et al., Limits of Cooperativity in a Structurally Modular Protein: Response of the Notch Ankyrin Domain to Analogous Alanine Substitut-ons in Each Repeat, J. Mol. BIoL (2002) 324, 373-386.*
Physical Changes with Aging, from Merck Manual, Jun. 2009, pp. 1-4, accessed Oct. 15, 2012.*
Siegel, Are Telomeres the Key to Aging and Cancer? from http://learn.genetics.utah.edu/content/begin/traits/telomeres/, pp. 1-3, accessed Oct. 15, 2012.*
Aubert et al, Telomeres and Aging, Physiol. Rev., 2008, 88, pp. 557-579.*
Callaway, Telomerase reverses ageing process: Nature News, 2010, pp. 1-13.*
Merck Manual Home Edition, Effects of Aging on the Skin, Oct. 2006, p. 1, accessed Apr. 9, 2012.*
Chronic Effects of Sunlight, from Merck Manual, Aug. 2007, pp. 1-2, accessed Aug. 23, 2012.*
Sequence listing of WO 2005/066337 A2, pp. 1-4, Jul. 2005.*
Michishita et al., *Nature*, vol. 452, pp. 492-496 (Mar. 27, 2008).
Kawahara, T.L.A. et al., "SIRT6 Links Histone H3 Lysine 9 Deacetylation to NF-κB-Dependent Gene Expression and Organismal Life Span," *Cell*, 136, pp. 62-74 (Jan. 9, 2009).
Amoyel et al., *Journal of Investigative Dermatology*, vol. 129 (Supplement 1s), p. S70 (2009).
Mostoslaysky, R. et al., *Cell*, 124, pp. 315-329 (Jan. 27, 2006).
Kullman et al., J. Biol. Chem., vol. 255, No. 17, pp. 8234-8238 (1980).

* cited by examiner

*Primary Examiner* — Julie Ha
*Assistant Examiner* — Li Ni Komatsu
(74) *Attorney, Agent, or Firm* — Thompson Hine L.L.P.

(57) ABSTRACT

The present invention relates to sirtuin 6 activating peptides derived from highly conserved regions of human Sirtuin (SIRT) proteins, and to a cosmetic or pharmaceutical composition comprising at least one sirtuin 6 activating peptide in a physiologically acceptable medium. The invention further relates to the utilization of a cosmetic composition to prevent and/or repair Deoxyribonucleic acid (DNA) degradation, improve telomere maintenance and reduce cellular senescence. The invention also applies to a cosmetic treatment process intended to prevent and/or treat the cutaneous signs of aging and photo aging.

15 Claims, 3 Drawing Sheets

FIG. 1

Multiple sequence alignment (CLUSTAL 2.0.12)

The three highly conserved regions appear highlighted below.

```
hSIRT2    ------------------------------------------------------------
hSIRT3    --------------MAFWGWRAAAALRLWGRVVERVEAGGGVGPFQACGCRLVLGGRDDV  46
hSIRT1    MADEAALALQPGGSPSAAGADREAASSPAGEPLRKRPRRDGPGLERSPGEPGGAAPEREV  60
hSIRT4    ------------------------------------------------------------
hSIRT7    ---------------------------------MAAGGLSRSERKAAERVRRLREEQQ   25
hSIRT6    ------------------------------------------------------------
hSIRT5    ------------------------------------------------------------ hSIRT2    ----------MAEP-DPSHPLETQAG-KVQEAQDSDSDSEG------GAAGGEADMDFLR  42
hSIRT3    SAGLRGSHGARGEPLDPARPLQRPPRPEVPRAFRRQPRAAAPSFFFSSIKGGRRSISFSV 106
hSIRT1    PAAARGCPGAAAAALWREAEAEAAAAGGEQEAQATAAAGEGDN--GPGLQGPSREPPLAD 118
hSIRT4    --------------MKMSFALTFRSAKGRWIANPSQP--------------CSKASIGLFV 33
hSIRT7    RERLR-----QVSRILRKAAAERSAEEGRLLAESADLVTELQG-------RSRRREGLKR 73
hSIRT6    -----------------MSVNYAAGLSPYADK-----------------GKCGLPEIFD  25
hSIRT5    ---------------MRPLQIVPSRLISQLYCGLKPP-------------ASTRNQICLK 32 hSIRT2    NLFSQTLSLGSQKER--------------------------------------------  57
hSIRT3    GASSVVGSGGSSDK---------------------------------------------- 120
hSIRT1    NLYDEDDDDEGEEEEEAAAAAIGYRDNLLFGDEIITNGFHSCESDEEDRASHASSSDWTP 178
hSIRT4    PASPP-------------------------------------------------------  38
hSIRT7    RQEEVCD-----------------------------------------------------  80
hSIRT6    PPEE--------------------------------------------------------  29
hSIRT5    MARP--------------------------------------------------------  36 hSIRT2    ------------------------------LLDELTLEGVARYMQSE--------     74
hSIRT3    ------------------------------GKLSLQDVAELIRAR---------    135
hSIRT1    RPRIGPYTFVQQHLMIGTDPRTILKDLLPETIPPPELDDMTLWQIVINILSEPPKRKKRK 238
hSIRT4    ------------------------------LDPEKVKELQRFITLS--------      54
hSIRT7    ------------------------------DPEELRGKVRELASAVR------       97
hSIRT6    ------------------------------LERKVWELARLVWQS--------       44
hSIRT5    ------------------------------SSSMADFRKFFAKA--------        50
                                      :             .

hSIRT2    --------------RCRRVICLVGAGISTSAGIPDFRSPSTGLYD--NLEKYHLPYPEAIF 119
hSIRT3    --------------ACQRVVVMVGAGISTPSGIPDFRSPGSGLYS--NLQQYDLPYPEAIF 180
hSIRT1    DINTIEDAVKLLQECKKIIVLTGAGVSVSCGIPDFRS-RDGIYARLAVDFPDLPDPQAMF 297
hSIRT4    --------------KRLLVMTGAGISTESGIPDYRSEKVGLYAR--TDRRPIQHGDFVR  97
hSIRT7    --------------NAKYLVVYTGAGISTAASIPDYRG-PNGVWT-------LLQKGRSVS 136
hSIRT6    --------------SSVVFHTGAGISTASGIPDFRG-PHGVWT--------MEERGLAP  80
hSIRT5    --------------KHIVIISGAGVSAESGVPTFRG-AGGYWR--KWQAQDLATPLAFA  92
                        ::   ***:*.  ..:* :*.    *  :            :

hSIRT2    EISYFKKHPEPFFALAKELYPGQFKPTICHYFMRLLKDKGLLLRCYTQNIDTLERIAGLE 179
hSIRT3    ELPFFFHNPKPFFTLAKELYPGNYKPNVTHYFLRLLHDKGLLLRLYTQNIDGLERVSGIP 240
hSIRT1    DIEYFRKDPRPFFKFAKEIYPGQFQPSLCHKFIALSDKEGKLLRNYTQNIDTLEQVAGIQ 357
hSIRT4    SAPIRQRYWARNFVGWPQFSS--HQPNPAHWALSTWEKLGKLYWLVTQNVDALHTKAGSR 155
hSIRT7    AADLS---------------EAEPTLTHMSITRLHEQKLVQHVVSQNCDGLHLRSGLP 179
hSIRT6    KFDTTFES--------------ARPTQTHMALVQLERVGLLRFLVSQNVDGLHVRSGFP 125
hSIRT5    HNPSRVWEFYHYRREVMGSKEPNAGHRAIAECETRLGKQGRRVVVITQNIDELHRKAGTK 152
                                                          :** *  *.  :*
```

FIG. 1 cont.

```
hSIRT2  QEDLVEAKGTFYTSHCVSASCRHEYPLSW-MKEKIFSEVTPKCEDCQS--------LVKP 230
hSIRT3  ASKLVEAKGTFASATCT--VCQRPFPGED-IRADVMADRVPRCPVCTG--------VVKP 289
hSIRT1  R--IIQCKGSFATASCL--ICKYKVDCEA-VRGDIFNQVVPRCPRCPADEP---LAIMKP 409
hSIRT4  R--LTELKGCMDRVLCLD--CGEQTPRGV-LQERFQVLNPTWSAEAHG--------LAPD 202
hSIRT7  RTAISELKGNMYIEVCTSCVPNREYVRVFDVTERTALHRFQTGRTCHKCG-----TQLRD 234
hSIRT6  RDKLAELKGNMFVEEECAK--CKTQYVRDTVVGTMGLKATGRLCTVAKARGLRACRGELRD 183
hSIRT5  N--LLEIKGSLFKTRCTS------------CGVVAENYKSPICPALSG--------KGAP 190
            :  :  **  :        * hSIRT2  DIVFFGES-LPARFFS--CMQSDFLKVDLLLVMGTSLQVQ---PFASLISKAPLSTPRLL 284
hSIRT3  DIVFFGEP-LPQRFLL--HVV-DFPMADLLLILGTSLEVE---PFASLTEAVRSSVPRLL 342
hSIRT1  EIVFFGEN-LPEQFHR--AMKYDKDEVDLLIVIGSSLKVR---PVALIPSSIPHEVPQIL 463
hSIRT4  GDVFLSEE-QVRSFQVPTCVQCGGHLKPDVVFFGDTVNPD---KVDFVHKRVKEADSLLV 258
hSIRT7  TIVHFGERGTLGQPLNWEAATEAASRADTILCLGSSLKVLKKYPRLWCMTKPPSRRPKLY 294
hSIRT6  TILDWEDS-LPDRDLA--LADEASRNADLSITLGTSLQIR---PSGNLPLATKRRGGRLV 237
hSIRT5  EPGTQDASIPVEKLPRCEEAGCGGLLRPHVVWFGENLDPA---ILEEVDRELAHCDLCLV 247
                      :  :*  .: .                             :

hSIRT2  INKF-------------------------KAGQSDPFLGMIMGLGGGMDFDSKKAYRDVAW 320
hSIRT3  INRD-------------------------LVGP-------------LAWHPR--SRDVAQ 362
hSIRT1  INREPLPELHFDVELLGDCDVIINELCHRLGGEYAKLCCNPVKLSEITEKPPRTQKELAY 523
hSIRT4  VGSS-------------------------------LQVYSGYRFILTAWEKKLPIAILN 286
hSIRT7  IVNLQWTP---------------------KDDWAALKLFGKCDDVMRLLMAELGLEIPA 332
hSIRT6  IVNLQP-----------------------TKHDRHADLRIEGYVDEVMTRLMEHLGLEIPA 275
hSIRT5  VGTS--------------------------------SVVYPAAMFAPQVAARGVPVAE 273
         :                                            :        :

hSIRT2  LGECDQG--------------------CLALAELLGWKKELEDLVRREHASIDAQSGAG 359
hSIRT3  LGDVVHG--------------------VESLVELLGWIEEMRDLVQRETGKLDG----- 396
hSIRT1  LSELPPTPLHVSEDSSSPERTSPPDSSVIVTLLDQAAKSNDDLDVSESKGCMEEKPQEVQ 583
hSIRT4  IGPTRSD--------------------DLACLKLNSRCGELLPLIDPC----------- 314
hSIRT7  YSRWQDP--------------------IFSLATPLRAGEEGSHSRKSLCRSREEAPPG 370
hSIRT6  WDGPRVLER-------------ALPPLPRPPTPKLEPKEESPTRINGSIPAGPKQEPCA 321
hSIRT5  FNTETTP--------------------ATNRFRFHFQGPCGTTLPEALACHENETVS- 310 hSIRT2  VPNPSTSASPKKSPPPAKDEARTTEREKPQ------------------------- 389
hSIRT3  ---------PDK------------------------------------------- 399
hSIRT1  TSRNVESIAEQMENPDLKNVGSSTGEKNERTSVAGTVRKCWPNRVAKEQISRRLDGNQYL 643
hSIRT4  -------------------------------------------------------
hSIRT7  DRGAPLSSAPILGGWFGRGCTKRTKRKKVT-------------------------- 400
hSIRT6  QHNGSEPASPKRERPTSPAPHRPPKRVKAKAVPS---------------------- 355
hSIRT5  ------------------------------------------------------- hSIRT2  -------------------------------------------------------
hSIRT3  -------------------------------------------------------
hSIRT1  FLPPNRYIFHGAEVYSDSEDDVLSSSCGSNSDSGTCQSPSLEEPMEDESEIEEFYNGLE 703
hSIRT4  -------------------------------------------------------
hSIRT7  -------------------------------------------------------
hSIRT6  -------------------------------------------------------
hSIRT5  ------------------------------------------------------- hSIRT2  ----------------------------------------------
hSIRT3  ----------------------------------------------
hSIRT1  DEPDVPERAGGAGFGTDGDDQEAINEAISVKQEVTDMNYPSNKS 747
hSIRT4  ----------------------------------------------
hSIRT7  ----------------------------------------------
hSIRT6  ----------------------------------------------
hSIRT5  ----------------------------------------------
```

SIRTUIN 6 ACTIVATING PEPTIDES AND COSMETIC OR PHARMACEUTICAL COMPOSITION CONTAINING THEM

RELATED APPLICATIONS

This application claims priority to French Patent Application Serial No. FR 10 02698, filed Jun. 29, 2010 under the original title "Nouveaux peptides activateurs de la sirtuine 6 et composition cosmétique ou pharmaceutique les comprenant," hereby incorporated by reference.

FIELD OF THE INVENTION

The present invention is situated in the cosmetic and pharmaceutical field, and more particularly in the dermatology field. The present invention relates to sirtuin 6 (SIRT6) activating peptides, derived from highly conserved regions of human SIRT proteins.

The present invention also relates to a cosmetic or pharmaceutical composition, comprising a SIRT6 activating peptide, used alone or in combination with at least one other active agent, in a physiologically acceptable medium. The invention also relates to the utilization of this novel peptide as an active agent in a cosmetic composition. The invention further relates to the utilization of a cosmetic composition to prevent and/or repair DNA degradation, improve telomere maintenance and reduce cellular senescence. Lastly, the invention applies to a cosmetic treatment process intended to prevent and/or treat the cutaneous signs of aging and photo aging, according to which an effective quantity of active agent, or a composition containing the active agent, is applied to the areas to be treated.

BACKGROUND OF THE INVENTION

Aging corresponds to the set of physiological processes that modify the structure and functions of the organism according to the time and stresses undergone. Intrinsic aging due to genetic factors and biochemical modifications that take place during states of fatigue and stress and hormonal changes such as pregnancy, etc., may be distinguished from extrinsic aging due to environmental factors to which the organism is subjected throughout its life, such as pollution, sunlight, disease, lifestyle, etc. Aging is a slow and progressive process that affects all cells and organs. Thus this applies to the skin, which constitutes a barrier between the external environment and the inner medium and protects the organism against external stresses. During aging, the appearance of the skin changes and thus wrinkles and fine lines, hyper- or hypopigmentation spots, dryness and even dehydration of the skin, thinning of the epidermis, elastosis, etc., may appear.

Intrinsic aging is closely linked to the repeated divisions of cells. Thus, in human somatic cells, telomeres shorten the rhythm of cellular division, until dysfunctional telomeres appear that induce senescence or apoptosis, depending on the cellular type. This phenomenon constitutes the biological clock that explains the fact that human somatic cells are programmed for a limited number of divisions.

Cellular senescence phenomena are accelerated by oxidative damage, particularly in areas of the body where the skin is exposed to the sun; Photo aging is then superimposed on intrinsic aging. Oxidative damage is promoted by various agents, both endogenous (metabolism, inflammation, redox cycles) and exogenous, such as UV radiation and ionizing radiation, tobacco abuse and various molecules supplied by the diet (toxic metals, alcohol). Damage caused by oxidative stress also reaches the DNA and lipids and proteins. At the DNA level, oxidative stress causes many structural modifications (mutations, cleavage, covalent protein cross-links). Oxidized bases, such as 8-oxo-guanine, increase with age and may reach up to 10,000 bases per day and per cell.

To combat aging, it is therefore of interest to identify novel compounds capable of both combating localized damage caused to the DNA by oxidative stress and slowing down cellular senescence by promoting telomere stability.

Such being the case, the inventors have recently identified an interesting molecular target capable of fulfilling these various functions.

SIRT proteins are nuclear or mitochondrial proteins, bearing a NAD+dependent deacetylase function and belonging to the sirtuin family. The deacetylase or mono-ADP-ribosyltransferase activity of sirtuins enables them to modulate the acetylation level of some histones, which suggests their involvement, particularly with 1, 2 and 3 sirtuins, in the regulation of epigenetic phenomena.

The human sirtuin family comprises 7 proteins, very conserved throughout evolution, named SIRT1 to SIRT7.

SIRT6 is a nuclear sirtuin specifically associated with telomere chromatin and plays a role in the maintenance and stabilization of telomeric structures (Michishita et al. Nature. 2008 Mar. 27; 452(7186):492-6). Thus, in the mouse invalidated for the SIRT6 gene, premature aging and a short lifespan are observed, as well as an increase in the replicative senescence of keratinocytes (Kawahara T L et al. Cell. 2009 Jan. 9; 136(1):62-74).

Telomeres are structures that cover the ends of chromosomes and protect chromosomes against enzymatic degradation, recombination and interchromosomal fusion. In humans, these structures are constituted of a DNA sequence repeated thousands of times, associated with specific proteins, such as TRF1 and TRF2. Recent studies have shown that the TRF2 expression declines during cell aging (Amoyel et al., J. Invest. Dermatol. April 2009; 129 (Supplement 1s), s70).

On the other hand, SIRT6 plays an important role in DNA repair by bases excision, a DNA repair mechanism utilized by the cell when the DNA has been damaged by oxidants. These discoveries suggest that SIRT6 is necessary for regulating genome integrity and aging phenomena and may be directly involved in the increase of cellular longevity (Mostoslaysky et al., Cell. 2006 Jan. 27; 124(2):315-29).

It is known that the utilization of SIRT1 protein activating peptides (FR 2883751, FR 2883752, FR 2883753, FR 2883754), enables cosmetic or pharmaceutical compositions useful for protecting the skin and combating aging to be prepared, or else that certain SIRT7 inducer pharmaceutical compounds are useful for treating age-related diseases (EP 1955715). However, to date, no peptide compound capable of activating the SIRT6 protein in skin cells has been described, while the need for this type of skin care exists.

SUMMARY

In one aspect, a peptide derived from the peptide sequence of highly conserved regions of human SIRT proteins is disclosed herein. The peptide has the general formula (I):

$$R_1\text{-}(AA)_n\text{-}X_1\text{—}X_2\text{—}X_3\text{—}X_4\text{—}X_5\text{—}X_6\text{-}(AA)_p\text{-}R_2 \qquad (I)$$

in which,
$X_1$ is glycine or threonine or histidine,
$X_2$ is alanine or glutamine or glycine,
$X_3$ is glycine or asparagine or serine,
$X_4$ is valine or isoleucine or leucine, $X_5$ is serine or aspartic acid or phenylalanine,
$X_6$ is alanine or glutamic acid or lysine,
and
when $X_1$ is glycine then $X_2$ is alanine and $X_3$ is glycine,
when $X_1$ is threonine then $X_3$ is asparagine,
when $X_1$ is histidine then $X_2$ is glycine,
AA represents any amino acid and n and p are integers between 0 and 2,
$R_1$ represents the primary amino function of the N-terminal amino acid, free or substituted by an acyl type group having either an alkyl chain from $C_1$ to $C_{30}$, saturated or unsaturated, that may be an acetyl group, or an aromatic group that may be chosen from among a benzoyl, tosyl or benzyloxycarbonyl type group, and
$R_2$ represents the hydroxyl group of the carboxyl function of the C-terminal amino acid, free or substituted by a group that may be chosen from among an alkyl chain from $C_1$ to $C_{30}$, or an $NH_2$, NHY or NYY group with Y representing an alkyl chain from $C_1$ to $C_4$.

The peptide may correspond to one of the following sequences:

```
                                            (SEQ ID No. 1)
    Glu-Ile-His-Gly-Ser-Leu-Phe-Lys-NH2

(SEQ ID No. 2)
    His-Gly-Ser-Leu-Phe-Lys-NH2

(SEQ ID No. 3)
    Leu-Val-Gly-Ala-Gly-Val-Ser-Ala-NH2

(SEQ ID No. 4)
    Gly-Ala-Gly-Val-Ser-Ala-Glu (SEQ ID No. 5)
    Gly-Ala-Gly-Val-Ser-Ala-Glu-NH2

(SEQ ID No. 6)
    Thr-Gln-Asn-Ile-Asp-Glu-Leu (SEQ ID No. 7)
    Thr-Gln-Asn-Ile-Asp-Glu-Leu-NH2

(SEQ ID No. 8)
    Val-Ile-Thr-Gln-Asn-Ile-Asp-Ala-NH2.
```

In another aspect, compositions were prepared that include the peptide discussed above.

BRIEF DESCRIPTION OF THE DRAWINGS

FIG. 1 is an alignment of human SIRT protein peptide sequences (the alignment was carried out by using the ClustalW2 multiple peptide sequence alignment program from the European Bioinformatics Institute);

DISCLOSURE OF THE INVENTION

Figure 2:
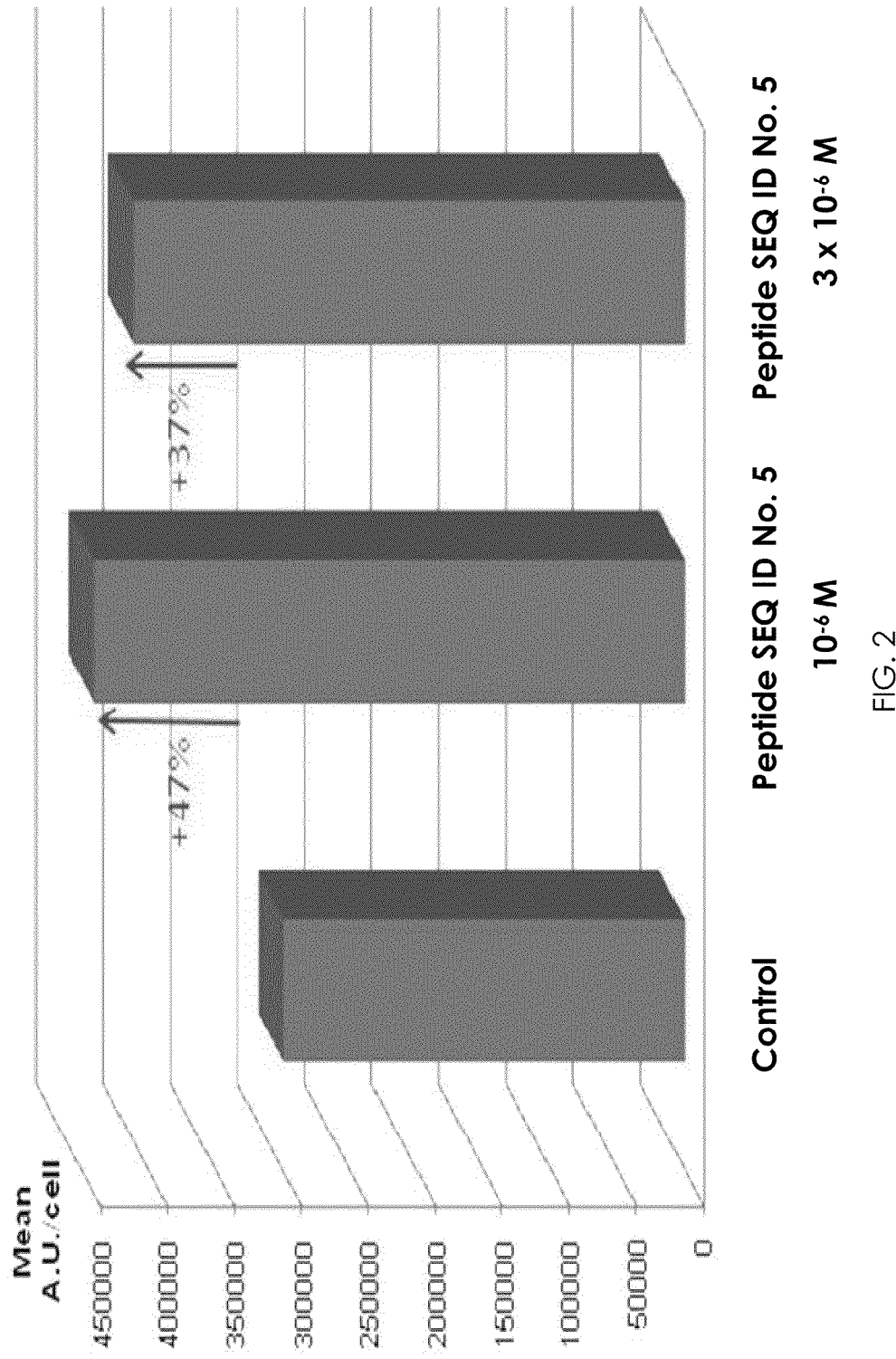
FIG. 2 is a quantification of sirtuin 6 (SIRT6) immunolabelling in normal human fibroblasts, treated 24 hours by the peptide SEQ ID No. 5.

The inventors have demonstrated that peptides derived from highly conserved regions of human SIRT proteins of the following general formula (I):

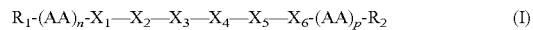

were very good SIRT6 activating agents, and would enable DNA degradation caused by external stresses and particularly by UV radiation to be prevented and/or effectively repaired, telomere maintenance to be improved and cellular senescence to be reduced. Consequently, these peptides are suitable for combating aging and photo aging of the skin.

Peptides according to the invention are characterized by the fact that they: (1) activate SIRT6 expression in skin cells; (2) reduce DNA degradation of skin cells subjected to UVB radiation; (3) promote the protection of skin cells subjected to oxidative stress; (4) stimulate the expression of TRF2 protein, specifically associated with telomeres; (5) increase the expression of proteins from the extracellular matrix by fibroblasts; and (5) optimize the barrier function of the epidermis.

"Peptide or SIRT6 activating active agent or active agent capable of activating human SIRT6" is understood to refer to any peptide of general formula (I) capable of increasing the quantity of SIRT6 present in the cell, or by increasing protein synthesis by direct or indirect modulation of the gene expression, or by other biological processes such as protein stabilization or else messenger RNA transcript stabilization.

"Skin" is understood to refer to all of the covering tissues constituting the skin, mucous membranes and epithelial appendages.

Alignment of peptide sequences of 7 proteins from the SIRT family was carried out by using the ClustalW2 multiple peptide sequence alignment program from the European Bioinformatics Institute presented in FIG. 1. Optimal alignment shows three highly conserved regions.

"Highly conserved region of human SIRT proteins" is understood to refer to peptide sequences comprising at least 2 absolutely identical consecutive amino acids in the 7 sirtuins of the family, when the sequences have been aligned on the basis of the highest homology. The first highly conserved region comprises the Gly-Ala-Gly peptide sequence. The second highly conserved region comprises the Gln-Asn peptide sequence. The third highly conserved region comprises the His-Gly peptide sequence.

Thus, the first object of the invention is a peptide of 6 to 10 amino acids, derived from the peptide sequence of a highly conserved region of human SIRT proteins that responds to general formula (I):

$$R_1\text{-}(AA)_n\text{-}X_1\text{—}X_2\text{—}X_3\text{—}X_4\text{—}X_5\text{—}X_6\text{-}(AA)_p\text{-}R_2 \qquad (I)$$

in which, $X_1$ is glycine or threonine or histidine, $X_2$ is alanine or glutamine or glycine, $X_3$ is glycine or asparagine or serine, $X_4$ is valine or isoleucine or leucine, $X_5$ is serine or aspartic acid or phenylalanine, $X_6$ is alanine or glutamic acid or lysine, and when $X_1$ is glycine then $X_2$ is alanine and $X_3$ is glycine, when $X_1$ is threonine then $X_3$ is asparagine, or when $X_1$ is histidine then $X_2$ is glycine, and AA represents any amino acid, or one of its derivatives, and n and p are integers between 0 and 2, and $R_1$ represents the primary amino function of the N-terminal amino acid, free or substituted by an acyl type group having either an alkyl chain from $C_1$ to $C_{30}$, saturated or unsaturated, that may be an acetyl group, or an aromatic group that may be chosen from among a benzoyl, tosyl or benzyloxycarbonyl type group, and $R_2$ represents the hydroxyl group of the carboxyl function of the C-terminal amino acid, free or substituted by a group that may be chosen from among an alkyl chain from $C_1$ to $C_{30}$, or an $NH_2$, NHY or NYY group with Y representing an alkyl chain from $C_1$ to $C_4$.

Said sequence of general formula (I) is constituted of 6 to 10 residues of amino acids.

According to a particularly preferred embodiment of the invention, the peptide has the sequence:

```
                                            (SEQ ID No. 1)
    Glu-Ile-His-Gly-Ser-Leu-Phe-Lys-NH2

(SEQ ID No. 2)
    His-Gly-Ser-Leu-Phe-Lys-NH2
```

-continued

Leu-Val-Gly-Ala-Gly-Val-Ser-Ala-NH$_2$ (SEQ ID No. 3)

Gly-Ala-Gly-Val-Ser-Ala-Glu (SEQ ID No. 4)

Gly-Ala-Gly-Val-Ser-Ala-Glu-NH$_2$ (SEQ ID No. 5)

Thr-Gln-Asn-Ile-Asp-Glu-Leu (SEQ ID No. 6)

Thr-Gln-Asn-Ile-Asp-Glu-Leu-NH$_2$ (SEQ ID No. 7)

Val-Ile-Thr-Gln-Asn-Ile-Asp-Ala-NH$_2$ (SEQ ID No. 8)

According to a particularly interesting embodiment, the peptide corresponds to the SEQ ID No. 4 or to the SEQ ID No. 5.

According to another particularly interesting embodiment, the peptide corresponds to the SEQ ID No. 6 or to the SEQ ID No. 7.

The amino acids, constituting the peptide according to the invention and designated by the terms AA or X, may be under isomeric configuration L- and D-. Preferentially, the amino acids are in L form.

The term "peptide" designates a linkage of two or more amino acids interlinked by peptide linkages or by modified peptide linkages.

"Peptide" is also understood to refer to the natural or synthetic peptide of the invention as described, or at least one of its fragments, whether obtained by proteolysis or synthetically, or else any natural or synthetic peptide whose sequence is partially or totally constituted by the sequence of the peptide previously described.

The peptide derivatives particularly relate to amino acids interconnected by a pseudo-peptide linkage. "Pseudo-peptide linkage" is understood to refer to all types of linkages capable of replacing "conventional" peptide linkages.

So as to improve resistance to degradation, it may be necessary to use a protected form of the peptide according to the invention. Preferably, to protect the primary amine function of the N-terminal amino acid, a substitution by an $R_1$ group of the acyl type having an alkyl chain from $C_1$ to $C_{30}$, saturated or unsaturated, that may be chosen from among an acetyl group or an aromatic group, may be utilized. Preferably, to protect the carboxyl function of the C-terminal amino acid, a substitution by an $R_2$ group of the $C_1$ to $C_{30}$ alkyl chain type, or an $NH_2$, NHY or NYY group with Y representing an alkyl chain from $C_1$ to $C_4$ is utilized. The peptide according to the invention may be protected at the region of the N-terminal end, C-terminal end or at the region of the two ends.

Thus, the invention relates to a composition such as previously defined, characterized by the fact that the peptide of SEQ ID No. 1 to SEQ ID No. 8 is in protected or unprotected form.

The peptide of general formula (I) according to the invention may be obtained either by conventional chemical synthesis (in solid phase or in homogeneous liquid phase), or by enzymatic synthesis (Kullman et al., J. Biol. Chem. 1980, 225, 8234), from constituent amino acids.

The peptide according to the invention may be of natural or synthetic origin. Preferentially, according to the invention, the peptide is of synthetic origin, obtained by chemical synthesis.

According to the invention, the active agent may be a single peptide, a mixture of peptides or peptide derivatives.

The peptide according to the invention is advantageously solubilized in one or more physiologically suitable solvents, such as water, glycerol, ethanol, propanediol, butylene glycol, dipropylene glycol, ethoxylated diethylene glycol or propoxylated diethylene glycol, cyclic polyols or any mixture of these solvents. The diluted peptide is then sterilized by sterile filtration.

After this dilution step, the peptide may be encapsulated or included in a cosmetic or pharmaceutical carrier such as liposomes or any other microcapsule utilized in the cosmetic field or adsorbed on powdery organic polymers, mineral supports such as talcs and bentonites.

"Physiologically suitable" is understood to mean that the solvent chosen is suitable for entering in contact with the skin without causing toxicity or intolerance reactions.

The peptide according to the invention may be utilized as a medication.

The second object of the invention is a cosmetic or pharmaceutical, in particular a dermatological composition comprising, in a physiologically suitable medium, a peptide of general formula (I) as a human SIRT6 activating active agent.

According to an advantageous embodiment of the invention, the active agent according to the invention is present in the compositions of the invention at a concentration of between approximately $10^{-9}$ M and $10^{-3}$ M, and preferentially at a concentration of between $2 \times 10^{-8}$ M and $10^{-5}$ M with relation to the total weight of the final composition.

This range of concentrations represents the effective quantity of active agent corresponding to the quantity necessary to obtain the desired result, that is, to activate the SIRT6, reduce DNA degradation and improve telomere maintenance.

In a preferred manner, the composition according to the invention is present in a form suitable for topical application comprising a medium that is physiologically suitable for the skin. "Physiologically suitable" is understood to refer to media that are suitable for a use in contact with the skin or with human epithelial appendages, without risk of toxicity, incompatibility, instability, allergic response or other secondary effects.

"Topical application" is understood to refer to the act of applying or spreading the active agent according to the invention, or a composition containing the agent, to or on the surface of the skin.

The compositions intended to be applied on the skin may be present in the form of an aqueous or hydroalcoholic solution, water in oil emulsion or oil in water emulsion, microemulsion, aqueous or anhydrous gel, serum, or else vesicle dispersion, patch, cream, spray, ointment, pomade, lotions, colloid, solution, suspension or other forms.

These compositions may particularly be present in the form of an aqueous solution, hydroalcoholic or oily solution; an oil in water emulsion, water in oil emulsion or multiple emulsions. They may also be present in the form of creams, suspensions or else powders, suitable for application on the skin, mucous membranes, lips and/or epithelial appendages. These compositions may be more or less fluid and have the appearance of a cream, lotion, milk, serum, pomade, gel, paste or foam. They may also be present in solid form, such as a stick, or may be applied on the skin in aerosol form. They may be utilized as a care product and/or as a skin makeup product.

In addition, any of the compositions disclosed herein may comprise any additive commonly utilized in the contemplated field of application as well as the adjuvants necessary for their formulation, such as co-solvents (ethanol, glycerol, benzyl alcohol, humectants, etc.), thickeners, diluents, emulsifiers, antioxidants, colorants, sunscreens, pigments, fillers, preservatives, fragrances, odor absorbers, essential oils, trace elements, essential fatty acids, surface active agents, film-forming polymers, chemical or mineral filters, moisturizing agents or thermal waters, etc. For example, one may include hydro-soluble polymers of the natural polymer type, such as polysaccharides or polypeptides, cellulosic derivatives of the methylcellulose type or hydroxypropylcellulose type, or else synthetic polymers, poloxamers, carbomers, siloxanes, PVA or PVP and particularly the polymers sold by the ISP company.

In all cases, the person skilled in the art will make sure that these adjuvants as well as their proportions are chosen so as to not harm the desired advantageous properties of the composition according to the invention. These adjuvants may, for example, be present at concentrations ranging from about 0.01 to about 20% of the total weight of the composition. When the composition of the invention is an emulsion, the fatty phase may represent from about 5 to about 80% by weight and preferably from about 5 to about 50% by weight with relation to the total weight of the composition. The emulsifiers and co-emulsifiers utilized in the composition will be chosen from among those conventionally utilized in the field under consideration. For example, they may be utilized in a proportion going from about 0.3 to about 30% by weight with relation to the total weight of the composition.

It is understood that the active agent according to the invention may be utilized alone or in combination with other active agents. Advantageously, the usable compositions according to the invention contain, also, at least one other active agent intended to promote the action of the active agent according to the invention and intended, in particular, for the prevention and/or treatment of age-related disorders. In a non-limiting manner, the following classes of ingredients may be cited: other peptide active agents, vegetable extracts, cicatrizant, anti-age, anti-wrinkle, smoothing, anti-radical, anti-UV agents, agents stimulating the synthesis of dermal macromolecules or energy metabolism, moisturizing, antibacterial, antifungal, anti-inflammatory, anesthetic agents, agents modulating cutaneous differentiation, pigmentation or depigmentation, agents stimulating nail or hair growth. In one embodiment, an anti-radical or antioxidant agent, or an agent stimulating the synthesis of dermal macromolecules, or else an agent stimulating energy metabolism will be utilized.

In another embodiment, the composition may comprise, in addition to the peptide disclosed herein, at least one cytochrome c activating compound, at least one moisturizing compound, such as an aquaporin activating compound, at least one sirtuin activating compound and in particular the peptides cited in patents FR 2 883754, US11/910,098, EP 1868631, incorporated by reference herein, at least one compound that increases cell adhesion, at least one compound that increases the production of matrix proteins such as collagen, fibronectin, laminin, mucopolysaccharide, at least one compound modulating proteasome activity, at least one compound modulating the circadian rhythm, at least one compound modulating HSP proteins, at least one compound that increases cell energy, at least one compound modulating skin pigmentation, at least one coenzyme Q10 activating compound, at least one compound improving the barrier function, such as transglutaminase activating compounds or HMG-CoA reductase activating compounds, at least one mitochondrial protector compound, at least one compound protecting or modulating the adult somatic cells of the epidermis or dermis, at least one compound protecting or repairing DNA degradation, and combinations thereof.

Said compounds above may be of natural origin, such as vegetable, animal or microorganism peptide hydrolysates, or else of synthetic origin, such as peptides.

Independently of their functions, the other active agents associated with the active agent in the composition may have very diverse chemical structures. In a non-limiting manner the other active agents may include other peptides, vitamin C and its derivatives, vitamins from group B, DHEA (dihydroepiandrosterone), phytosterols, salicylic acid and its derivatives, retinoids, flavonoids, sugar amines, azole compounds, metallic salts, peptide extracts of natural origin or else natural or synthetic polymers.

Another object of the invention is a pharmaceutical composition comprising, in a physiologically acceptable medium, the peptide according to the invention as a medication. The pharmaceutical composition according to the invention will improve dermatological symptoms connected with premature aging or photo aging, among which xerosis, depigmentation or conversely brown spots, keratosis, etc.

Advantageously, according to this form of the invention, the compositions will be suitable for oral administration for pharmaceutical use. Thus, the compositions may, in particular, be present in the form of tablets, capsules, gel capsules, chewable pastes, powders to consume as is or to be mixed immediately before use with a liquid, syrup, gel or any other form known to the person skilled in the art. They will contain suitable formulation excipients, such as colorants, sweeteners, flavorings, bulking agents, binders and preservatives.

The third object of the invention is a cosmetic composition comprising the peptide of general formula (I), as an active agent, to prevent and/or repair DNA degradation. "Active agent to prevent and/or repair DNA degradation" is understood to refer to a peptide capable of limiting DNA degradation or promoting the repair of damage due to photochemical reactions between DNA bases.

The fourth object of the invention is a cosmetic composition comprising the peptide of general formula (I), as an active agent, to improve telomere maintenance and reduce cellular senescence. "Active agent to improve telomere maintenance and reduce cellular senescence" is understood to refer to a peptide capable of increasing the synthesis of proteins specifically associated with telomeres and participating in their stability, such as TRF2 and SIRT6.

The fifth object of the invention is the utilization of a cosmetic composition comprising the peptide of general formula (I) as an active agent to increase the expression of keratinocyte differentiation markers and to promote the expression of extracellular matrix proteins by fibroblasts of the skin. These particular properties of the active agent according to the invention, improve the quality of the dermis and thus the firmness of the skin, and optimize the barrier function of the epidermis.

The sixth object of the invention is the utilization of a composition comprising the peptide of general formula (I), as an active agent, to protect the skin against all types of external stresses. The expression "external stresses" is understood to refer to stresses that the environment may produce. By way of example, such stresses may include pollution, UV radiation or else irritating products such as surface active agents, preservatives or fragrances, or mechanical stresses, such as abrasions, shaving or epilation. Pollution is understood to refer to both "external" pollution, due for example to diesel particles, ozone or heavy metals and to "internal" pollution, that may be particularly due to the emissions from paint, adhesive or wallpaper solvents (such as toluene, styrene, xylene or benzaldehyde), or else to cigarette smoke.

In particular, the object of the invention is the utilization of a cosmetic composition comprising an effective quantity of peptide according to the invention to prevent or treat damage caused to the skin by exposure to UV radiation and by oxidative stress.

The seventh object of the invention is a cosmetic treatment method characterized in that a composition comprising an effective quantity of active agent according to the invention is topically applied to the skin to be treated to prevent and/or treat cutaneous signs of aging and photo aging. "Cutaneous signs of aging" is understood to refer to any modifications in the external appearance of the skin and epithelial appendages due to aging such as, for example, superficial roughness of the horny layer of the epidermis, wrinkles and fine lines, but also any internal modification of the skin that is not systematically manifested in a modified external appearance such as, for example, thinning of the dermis or any other internal degradation of the skin following exposure to UV radiation. In particular, the invention relates to a cosmetic treatment method intended to protect the skin against stresses due to UV radiation.

Other advantages and characteristics of the invention will more clearly appear upon reading the examples given for illustrative and non-limiting purposes.

EXAMPLE 1

Demonstration of the Activating Effect of Peptides SEQ ID No. 5 and SEQ ID No. 7 on Sirtuin 6 Expression The object of this study is to determine the influence of peptides SEQ ID No. 5 and SEQ ID No. 7 on Sirtuin 6 expression in human skin. To do this, specific labeling by immunofluorescence was carried out on normal human keratinocytes (NHK) culture and on normal human fibroblast cultures.

Protocol: NHK or normal human fibroblasts are treated once per day with a solution at $10^{-6}$M or at $3\times10^{-6}$M of peptide SEQ ID No. 5 or peptide SEQ ID No. 7.

Short-term treatment studies for 24, 48 and 72 hours were carried out.

Long-term treatment studies were also carried out between passage 5 and passage 17 (or 12 passages) for fibroblasts and between passage 3 and passage 5 (or 2 subcultures) for NHK.

For immunolabelling by anti SIRT6 antibodies, the cells are washed and fixed with paraformaldehyde at 3.7% for 10 minutes. The cells are then incubated in the presence of a specific anti SIRT6 antibody (Abeam, ref ab62738, polyclonal rabbit), and then a secondary suitable antibody, coupled with a fluorescent dye. After mounting in a particular medium, the slides are observed by epifluorescence microscope (Nikon Eclipse E 80i microscope). Fluorescence intensity is quantified by analyzing the image using the Image-Pro Analyser version 5 software.

Results: Under all the conditions tested, more intense fluorescence was observed in cultures treated by the peptide SEQ ID No. 5 and by the peptide SEQ ID No. 7 at $10^{-6}$M or at $3\times10^{-6}$ M than under the control conditions. In the fibroblasts, a maximum increase of 47% of the fluorescence is observed in the cells treated for 24 hours by $10^{-6}$ M of peptide SEQ ID No. 5, with relation to the control cells (FIG. 2). In the NHK, a maximum increase of 35% of the fluorescence is observed in cells treated for 72 hours by $3\times10^{-6}$M of peptide SEQ ID No. 5, with relation to the control cells. The fluorescence increase is dose-dependent for the first 72 hours. On the other hand, the increase in SIRT6 expression is maintained during long-term treatment for both types of cells tested.

Conclusions: Peptides SEQ ID No. 5 and SEQ ID No. 7 increase sirtuin 6 expression very significantly in normal human fibroblasts and NHK in short-term cultures. In addition, the sirtuin 6 expression stimulation effect is maintained for the long term.

EXAMPLE 2

Demonstration of the Activating Effect of Peptide SEQ ID No. 4 on TRF2 Protein Expression The goal of this study is to determine the influence of peptide SEQ ID No. 4 on TRF2 protein expression in human skin, a protein specifically associated with telomeres and involved in their maintenance. To do this, specific labeling by immunofluorescence was carried out on normal human keratinocytes (NHK) culture and on normal human fibroblast cultures on a long-term basis.

Protocol: NHK or normal human fibroblasts in culture are treated once per day with a solution at $10^{-6}$M or at $3\times10^{-6}$M of peptide SEQ ID No. 4, between passage 5 and passage 17 (or 12 passages) for fibroblasts and between passage 1 and passage 2 (or 1 passage and 10 days of treatment) for NHK.

For immunolabelling by anti TRF2 antibodies, the cells are washed and fixed with paraformaldehyde at 3.7% for 10 minutes. The cells are then incubated in the presence of a specific anti TRF2 antibody (Abeam, ref ab13579, polyclonal mouse), and then a secondary suitable antibody, coupled with a fluorescent dye. After mounting in a particular medium, the slides are observed by epifluorescence microscope (Nikon Eclipse E 80i microscope). Fluorescence intensity is quantified by analyzing the image using the Image-Pro Analyser version 5 software.

Results: Under all the conditions tested, more intense fluorescence was observed in cultures treated by the peptide SEQ ID No. 4 at $10^{-6}$ M or at $3\times10^{-6}$ M than under the control conditions. In the fibroblasts, a maximum increase of 63% of the fluorescence is observed in the cells treated for 12 subcultures by $10^{-6}$ M of peptide SEQ ID No. 4, with relation to the control cells. The fluorescence increase is dose-dependent. In the NHK, a maximum increase of 39% of the fluorescence is observed in cells treated for 10 days by $3\times10^{-6}$ M of peptide SEQ ID No. 4, with relation to the control cells. The fluorescence increase is dose-dependent.

Conclusions: Peptide SEQ ID No. 4 increases TRF2 protein expression very significantly in normal human fibroblasts and NHK, in a dose-dependent manner, in long-term cultures.

EXAMPLE 3

Demonstration of the Activating Effect of Peptide SEQ ID No. 5 On Epidermal Differentiation and the Barrier Function of the Epidermis The goal of this study is to determine the influence of peptide SEQ ID No. 5 on epidermal differentiation. To do this, the expression of the main epidermal differentiation markers, specifically expressed in the keratinocytes of suprabasal layers cultivated on a long-term basis, was studied. The markers tested are transglutaminase 1 and involucrin.

Protocol: NHK in culture are treated once per day with a solution at $10^{-6}$M or at $3\times10^{-6}$M of peptide SEQ ID No. 5, between passage 1 and passage 3 (or 2 passages and 11 days of treatment). The cells are then washed and fixed. After unmasking the specific sites, the cells are incubated in the presence of a specific antibody directed against TG1 (TEBU, ref sc-25786, polyclonal rabbit), a specific antibody directed against involucrin (Novocastra NCL-INV, mouse monoclonal, clone SYS), and then incubated in the presence of a suitable secondary antibody, coupled with a fluorescent dye. For greater ease of observation, the cell nuclei may be counterstained by DAPI (4',6' Di Amidino-2-Phenylindole), a fluorescent blue molecule capable of strongly bonding to DNA). After mounting in a particular medium, the slides are observed by epifluorescence microscope (Nikon Eclipse E 80i microscope).

Results: More intense fluorescence is observed in cultures and on the sections of skin treated by the peptide SEQ ID No. 5 at $10^{-6}$ M or at $3\times10^{-6}$ M than under the control conditions.

Conclusions: Peptide SEQ ID No. 5 at $10^{-6}$ M or at $3\times10^{-6}$ M improves NHK differentiation and this optimizes the barrier function of the epidermis.

EXAMPLE 4

Demonstration of the Activating Effect of Peptide SEQ ID No. 5 On the Expression of Dermal Extracellular Matrix Molecules The goal of this study is to determine the influence of peptide SEQ ID No. 5 on the expression of dermal extracellular matrix molecules. To do this, the expression of collagens I and III in normal human fibroblasts cultivated on a long-term basis was studied.

Protocol: Normal human fibroblasts are treated once per day with a solution at $10^{-6}$ M or at $3\times10^{-6}$ M of peptide SEQ ID No. 5, between passage 5 and passage 17 (or 12 passages). The cells are then washed and fixed with cold methanol for 5 minutes. After unmasking specific sites, the cells are incubated in the presence of a specific antibody directed against collagen I (TEBU, ref 600-401-103, polyclonal rabbit) or against collagen III (TEBU, ref 600-401-105, polyclonal rabbit), and then incubated in the presence of a suitable secondary antibody, coupled with a fluorescent dye. After mounting in a particular medium, the slides are observed by epifluorescence microscope (Nikon Eclipse E 80i microscope).

Results: More intense fluorescence is observed in cultures and on the sections of skin treated by the peptide SEQ ID No. 5 at $10^{-6}$ M or at $3\times10^{-6}$ M than under the control conditions.

Conclusions: Peptide SEQ ID No. 5 at $10^{-6}$ M or at $3\times10^{-6}$ M applied on a long-term basis increases the expression of collagen I and collagen III, two essential proteins from the dermal extracellular matrix.

EXAMPLE 5

Demonstration of the Effect of Peptide SEQ ID No. 5 on Damage Caused to the DNA by Uv Radiation The goal of this study is to determine the protective effect of peptide SEQ ID No. 5 on damage caused to the DNA by UV radiation. To do this, a comet assay, that enables damage caused to the DNA at the cellular level to be quantified, was performed.

Protocol: Normal human fibroblasts are cultured for 24 hours with the peptide of sequence SEQ ID No. 5 at a concentration of $10^{-6}$ M or $3\times10^{-6}$ M, and then irradiated with UVB radiation at a rate of 60 mJ/cm$^2$, and then treated again for 24 hours by the peptide at a concentration of $10^{-6}$ M or $3\times10^{-6}$ M. A control condition is carried out in the absence of treatment. The cells are then detached from their support by the trypsin, then centrifuged at 1200 rotations/min for 10 minutes in order to concentrate and count them.

A defined number of cells (25,000 cells) is then included in a Low Melting agarose gel at 0.75%, and then deposited on a glass slide previously covered with agarose at 1%. The slides are then immersed in a lysis solution for 1½ hours at 4° C., and then in an alkaline solution for 20 min at 4° C. The cells are thus lyzed and the DNA is denatured. The slides are immersed in an electrophoresis solution before applying an electrical field (20 V-250 mA). The DNA thus denatured is subjected to migration within the agarose gel at 4° C., for 30 min. The application of a DNA fluorescent dye, propidium iodide at 2 µg/ml, on the slides for 20 minutes enables the DNA, in the shape of comet tails if it has been damaged, to be observed with a microscope.

Quantification software enables the mean "Tail Moment" (or length of the comet tail) applied to each condition tested to be determined This parameter provides information on the level of DNA damage: the higher this parameter, the greater the DNA degradation.

Results: The results show a reduction of 24.8% of the Tail Moment when the cells are treated by the peptide of SEQ ID No. 5 at $3\times10^{-6}$ M, compared to the control conditions.

Conclusion: The DNA of the cells treated and then subjected to UVB radiation has undergone less damage than the DNA of the control cells. These results confirm the preventive protector and curative effect of the peptide of sequence SEQ ID No. 5 in relation to UVB radiation.

EXAMPLE 6

Demonstration of the Protective Effect of SEQ ID No. 5 During Oxidative Stress

The goal of this study is to determine the protective effect of peptide SEQ ID No. 5 on keratinocytes during oxidative stress. To do this, the expression of Sirtuin 6 was qualitatively and quantitatively evaluated by specific immunolabelling after oxidative stress by $H_2O_2$.

Protocol: The NHK in culture are treated for 24 hours with a solution at $10^{-6}$ M or $3\times10^{-6}$ M of peptide SEQ ID No. 5. The cells are then incubated in the presence of $H_2O_2$ at 2 mM, rinsed and then treated for another 24 hours with a solution at $10^{-6}$ M or $3\times10^{-6}$ M of peptide SEQ ID No. 5. A control that was not treated and not subjected to the $H_2O_2$ stress (control 0), as well as a control that was not treated but was subjected to the $H_2O_2$ stress (control 1) were carried out.

For immunolabelling by anti SIRT6 antibodies, the cells are washed and fixed with paraformaldehyde at 3.7% for 10 minutes. The cells are then incubated in the presence of a specific anti SIRT6 antibody (Abcam, ref ab62738, polyclonal mouse), and then a secondary suitable antibody, coupled with a fluorescent dye. After mounting in a particular medium, the slides are observed by epifluorescence microscope (Nikon Eclipse E 80i microscope). Fluorescence intensity is quantified by analyzing the image using the Image-Pro Analyser version 5 software.

Results: Quantitative analysis shows an increase of respectively 16% and 20% in SIRT6 expression when the NHK are treated by peptide SEQ ID No. 5 at $10^{-6}$ M or $3\times10^{-6}$ M, and subjected to a $H_2O_2$ stress, with relation to control 1.

Conclusions: The cells treated by peptide SEQ ID No. 5, preventively and subsequent to oxidative stress, have an SIRT6 protein content greater than that of the control cells.

These results confirm that the peptide of sequence SEQ ID No. 5 promotes NHK protection during oxidative stress.

EXAMPLE 7

Preparation of Compositions

TABLE 1

Sun protection cream

| Trade names | INCI names | Weight percent |
| --- | --- | --- |
| PHASE A | | |
| Demineralized water | Aqua (Water) | qsp |
| Pemulen TR1 | Acrylates/C10-30 Alkyl Acrylate Crosspolymer | 0.40 |
| Glycerin | Glycerin | 3.00 |
| Nipastat Sodium | Sodium Methylparaben (and) Sodium Ethylparaben (and) Sodium Butyl paraben (and) Sodium Propylparaben (and) Sodium Isobutylparaben | 0.15 |
| PHASE B | | |
| Parsol MCX | Ethylhexyl Methoxycinnamate | 7.50 |
| Eusolex 4360 | Benzophenone-3 | 3.00 |
| Parsol 1789 | Butyl Methoxydibenzoylmethane | 2.00 |
| Myritol 318 | Caprylic/Capric Triglyceride | 4.00 |
| Emulgade SEV | Hydrogenated Palm Glycerides (and) Ceteareth-20 (and) Ceteareth-12 (and) Cetearyl Alcohol | 5.00 |
| Propylparaben | Propylparaben | 0.15 |
| Nacol 16-98 | Cetyl Alcohol | 1.00 |
| PHASE C | | |
| TEA | Triethanolamine | 0.20 |
| PHASE D | | |
| Peptide SEQ ID No. 4 | | $3 \times 10^{-6}$M |
| Fragrance | Fragrance | qsp |
| Colorant | | qsp |

The constituents of phase A and phase B are heated separately between 70° C. and 75° C. Phase B is emulsified in phase A under stirring. Phase C is added at 45° C., by increasing the stirring. Phase D is then added when the temperature is below 40° C. The cooling is continued until 25° C. under intensive stirring.

TABLE 2

Anti-aging cream

| Trade names | INCI names | Weight percent |
| --- | --- | --- |
| PHASE A | | |
| Montanov 68 | Cetearyl Alcohol (and) Cetearyl Glucoside | 6.00 |
| Squalane | Squalane | 3.00 |
| Cetiol SB 45 | Butyrospermum Parkii (Shea Butter) | 2.00 |
| Waglinol 250 | Cetearyl Ethylhexanoate | 3.00 |
| Amerchol L-101 | Mineral Oil (and) Lanolin Alcohol | 2.00 |
| Abil 350 | Dimethicone | 1.50 |
| BHT | BHT | 0.01 |
| Coenzyme Q10 | Ubiquinone | 0.10 |

TABLE 2-continued

Anti-aging cream

| Trade names | INCI names | Weight percent |
| --- | --- | --- |
| Phase B | | |
| Avocado oil | Persea Gratissima (Avocado) Oil | 1.25 |
| Phenonip | Phenoxyethanol (and) Methylparaben (and) Ethylparaben (and) Butylparaben (and) Propylparaben (and) Isobutylparaben | 0.75 |
| Phase C | | |
| Demineralized water | Aqua (Water) | qsp |
| Butylene Glycol | Butylene Glycol | 2.00 |
| Glucam E10 | Methyl Gluceth-10 | 1.00 |
| Allantoin | Allantoin | 0.15 |
| Carbopol Ultrez 10 | Carbomer | 0.20 |
| Phase D | | |
| TEA | Triethanolamine | 0.18 |
| Phase E | | |
| Peptide SEQ ID No. 5 | | $1 \times 10^{-6}$M |
| GP4G | Water (and) Artemia Extract | 1.50 |
| Collaxyl | Water (and) Butylene Glycol (and) Hexapeptide-9 | 3.00 |
| Phase F | | |
| Fragrance | Fragrance | qsp |
| Colorant | | qsp |

Prepare and melt phase A at 65-70° C. Heat phase C to 65-70° C. Phase B is added to phase A just before emulsifying A into B. At approximately 45° C., the carbomer is neutralized by adding phase D. Phase E is then added under mild stirring and cooling is continued until 25° C. Phase F is then added if desired.

TABLE 3

Protective day cream

| Trade names | INCI names | Weight percent |
| --- | --- | --- |
| Phase A | | |
| Emulium Delta | Cetyl alcohol (and) Glyceryl Stearate (and) PEG-75 Stearate (and) Ceteth-20 (and) Steareth-20 | 4.00 |
| Lanette O | Cetearyl Alcohol | 1.50 |
| D C 200 Fluid/100cs | Dimethicone | 1.00 |
| DUB 810C | Coco Caprylate/Caprate | 1.00 |
| DPPG | Propylene Glycol Dipelargonate | 3.00 |
| DUB DPHCC | Dipentaerythrityl Hexacaprylate/Hexacaprate | 1.50 |
| Cegesoft PS6 | Vegetable Oil | 1.00 |
| Vitamin E | Tocopherol | 0.30 |
| Phenonip | Phenoxyethanol (and) Methylparaben (and) Ethylparaben (and) Butylparaben (and) Propylparaben (and) Isobutylparaben | 0.70 |
| Phase B | | |
| Demineralized water | Aqua | qsp 100 |
| Glycerin | Glycerin | 2.00 |
| Carbopol EDT 2020 | Acrylates/C10-30Alkyl Acrylate Crosspolymer | 0.15 |
| Keltrol BT | Xanthan Gum | 0.30 |

TABLE 3-continued

Protective day cream

| Trade names | INCI names | Weight percent |
|---|---|---|
| *Phase C* | | |
| Sodium Hydroxide (10% sol.) | Sodium Hydroxide | 0.30 |
| *Phase D* | | |
| Demineralized water | Aqua | 5.00 |
| Stay-C 50 | Sodium Ascorbyl Phosphate | 0.50 |
| *Phase E* | | |
| Butylene Glycol | Butylene Glycol | 2.00 |
| Dekaben CP | Chlorphenesin | 0.20 |
| *Phase F* | | |
| GP4G | Water (and) Artemia Extract | 1.00 |
| Peptide SEQ ID No.5 | | $2 \times 10^{-6}$M |

Prepare phase A and heat to 75° C. under stirring. Prepare phase B by dispersing the carbopol and then the xanthan gum under stirring. Let rest. Heat to 75° C. and then emulsify A into B under rotor stator stirring while maintaining the 75° C. Neutralize with phase C under rapid stirring. After cooling to 40° C., add phase D, and then phase E. Cooling is continued under mild stirring and phase F is added.

Applicants incorporate by reference the material contained in the accompanying computer readable Sequence Listing entitled "Bv_10_142_SEQII_ST25.txt", which was created on Sep. 18, 2013, and is 27,581 bytes in size, and hereby confirm that the information recorded in the computer readable form is identical to the written sequence listing.

What is claimed is:

1. A peptide comprising a peptide sequence of highly conserved regions of human Sirtuin (SIRT) proteins, of general formula (I):

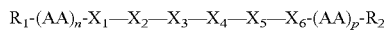

in which,
X$_1$ is glycine or threonine or histidine,
X$_2$ is alanine or glutamine or glycine,
X$_3$ is glycine or asparagine or serine,
X$_4$ is valine or isoleucine or leucine,
X$_5$ is serine or aspartic acid or phenylalanine,
X$_6$ is alanine or glutamic acid or lysine, and
when X$_1$ is glycine then X$_2$ is alanine and X$_3$ is glycine,
when X$_1$ is threonine then X$_3$ is asparagine,
when X$_1$ is histidine then X$_2$ is glycine,
AA is any amino acid and n and p are integers between 0 and 2,
R$_1$ is the primary amino function of the N-terminal amino acid, free or substituted by an acyl type group having either an alkyl chain from C$_1$ to C$_{30}$, saturated or unsaturated, an acetyl group, or an aromatic group chosen from among a benzoyl, tosyl or benzyloxycarbonyl type group, and
R$_2$ is the hydroxyl group of the carboxyl function of the C-terminal amino acid, free or substituted by a group chosen from among an alkyl chain from C$_1$ to C$_{30}$, or an NH$_2$, NHY or NYY group with Y representing an alkyl chain from C$_1$ to C$_4$,
wherein the peptide is one of the following sequences:

```
                                            (SEQ ID NO: 3)
    Leu-Val-Gly-Ala-Gly-Val-Ser-Ala-NH2

(SEQ ID NO: 4)
    Gly-Ala-Gly-Val-Ser-Ala-Glu (SEQ ID NO: 5)
    Gly-Ala-Gly-Val-Ser-Ala-Glu-NH2.
```

2. The peptide according to claim 1 wherein the peptide is (SEQ ID NO: 5) Gly-Ala-Gly-Val-Ser-Ala-Glu-NH$_2$.

3. The peptide according to claim 1, wherein the peptide is solubilized in one or more physiologically acceptable solvents selected from the group consisting of water, glycerol, ethanol, propanediol, propylene glycol, butylene glycol, dipropylene glycol, ethoxylated diethylene glycol or propoxylated diethylene glycol, cyclic polyols, white petroleum jelly, vegetable oil, and combinations thereof 4. A cosmetic composition comprising:
at least one peptide as defined in claim 1, as a Sirtuin 6 (SIRT6) activating agent, in a physiologically acceptable medium, wherein the peptide is present in the medium alone or in combination with at least one other active agent selected from the group consisting of vitamin C, vitamin B, dihydroepiandrosterone (DHEA), phytosterols, salicylic acid, retinoids, flavonoids, sugar amines, azole compounds, and metallic salts.

5. The composition according to claim 4, wherein said peptide is present at a concentration of between 10$^{-9}$ M and 10$^{-3}$ M in relation to the total weight of the final composition.

6. The composition according to claim 4, wherein said peptide is present at a concentration of between 2×10$^{-8}$ M and 10$^{-5}$ M in relation to the total weight of the final composition.

7. The composition according to claim 4, wherein the composition is a topical composition.

8. A cosmetic composition comprising:
a peptide comprising a peptide sequence of highly conserved regions of human Sirtuin (SIRT) proteins, of general formula (I):

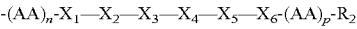

in which,
X$_1$ is glycine or threonine or histidine,
X$_2$ is alanine or glutamine or glycine,
X$_3$ is glycine or asparagine or serine,
X$_4$ is valine or isoleucine or leucine,
X$_5$ is serine or aspartic acid or phenylalanine,
X$_6$ is alanine or glutamic acid or lysine, and
when X$_1$ is glycine then X$_2$ is alanine and X$_3$ is glycine,
when X$_1$ is threonine then X$_3$ is asparagine,
when X$_1$ is histidine then X$_2$ is glycine,
AA is any amino acid and n and p are integers between 0 and 2,
R$_1$ is the primary amino function of the N-terminal amino acid, free or substituted by an acyl type group having either an alkyl chain from C$_1$ to C$_{30}$, saturated or unsaturated, an acetyl group, or an aromatic group chosen from among a benzoyl, tosyl or benzyloxycarbonyl type group, and
R$_2$ is the hydroxyl group of the carboxyl function of the C-terminal amino acid, free or substituted by a group chosen from among an alkyl chain from C$_1$ to C$_{30}$, or an NH$_2$, NHY or NYY group with Y representing an alkyl chain from C$_1$ to C$_4$;
wherein the peptide is one of the following sequences:

```
                                            (SEQ ID NO: 3)
    Leu-Val-Gly-Ala-Gly-Val-Ser-Ala-NH2

(SEQ ID NO: 4)
    Gly-Ala-Gly-Val-Ser-Ala-Glu (SEQ ID NO: 5)
    Gly-Ala-Gly-Val-Ser-Ala-Glu-NH2, and
``` a physiologically acceptable medium,
said cosmetic composition for repairing Deoxyribonucleic acid (DNA) degradation, for improving telomere maintenance, or for increasing the expression of keratinocyte differentiation markers and promoting the expression of extracellular matrix proteins by skin fibroblasts.

9. The composition according to claim 8 wherein the peptide is (SEQ ID NO: 5) Gly-Ala-Gly-Val-Ser-Ala-Glu-NH$_2$.

10. The composition according to claim 8, wherein the peptide is solubilized in one or more physiologically acceptable solvents selected from the group consisting of water, glycerol, ethanol, propanediol, propylene glycol, butylene glycol, dipropylene glycol, ethoxylated diethylene glycol or propoxylated diethylene glycol, cyclic polyols, white petroleum jelly, vegetable oil, and combinations thereof.

11. The composition according to claim 8, wherein said peptide is present at a concentration of between 10$^{-9}$ M and 10$^{-3}$ M in relation to the total weight of the final composition.

12. The composition according to claim 8, wherein said peptide is present at a concentration of between 2×10$^{-8}$ M and 10$^{-5}$ M in relation to the total weight of the final composition.

13. A method for treating cutaneous signs of aging and photo aging on skin, the method comprising:
topically applying, to skin to be treated, a composition comprising an effective quantity of a peptide comprising a peptide sequence of highly conserved regions of human Sirtuin (SIRT) proteins, of general formula (I):

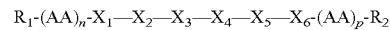

in which,
- $X_1$ is glycine or threonine or histidine,
- $X_2$ is alanine or glutamine or glycine,
- $X_3$ is glycine or asparagine or serine,
- $X_4$ is valine or isoleucine or leucine,
- $X_5$ is serine or aspartic acid or phenylalanine,
- $X_6$ is alanine or glutamic acid or lysine, and
- when $X_1$ is glycine then $X_2$ is alanine and $X_3$ is glycine,
- when $X_1$ is threonine then $X_3$ is asparagine,
- when $X_1$ is histidine then $X_2$ is glycine,
- AA is any amino acid and n and p are integers between 0 and 2,
- $R_1$ is the primary amino function of the N-terminal amino acid, free or substituted by an acyl type group having either an alkyl chain from $C_1$ to $C_{30}$, saturated or unsaturated, an acetyl group, or an aromatic group chosen from among a benzoyl, tosyl or benzyloxycarbonyl type group, and
- $R_2$ is the hydroxyl group of the carboxyl function of the C-terminal amino acid, free or substituted by a group chosen from among an alkyl chain from $C_1$ to $C_{30}$, or an $NH_2$, NHY or NYY group with Y representing an alkyl chain from $C_1$ to $C_4$, wherein the peptide is one of the following sequences:

```
                                             (SEQ ID NO: 3)
Leu-Val-Gly-Ala-Gly-Val-Ser-Ala-NH2

(SEQ ID NO: 4)
Gly-Ala-Gly-Val-Ser-Ala-Glu (SEQ ID NO: 5)
Gly-Ala-Gly-Val-Ser-Ala-Glu-NH2.
```

14. The method according to claim 13 wherein the peptide is (SEQ ID NO: 5) Gly-Ala-Gly-Val-Ser-Ala-Glu-$NH_2$.

15. The method according to claim 13, wherein the peptide is solubilized in one or more physiologically acceptable solvents selected from the group consisting of water, glycerol, ethanol, propanediol, propylene glycol, butylene glycol, dipropylene glycol, ethoxylated diethylene glycol or propoxylated diethylene glycol, cyclic polyols, white petroleum jelly, vegetable oil, and combinations thereof.

* * * * *

```
                         SEQUENCE LISTING

<160> NUMBER OF SEQ ID NOS: 15

<210> SEQ ID NO 1
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (8)..(8)
<223> OTHER INFORMATION: AMIDATION

<400> SEQUENCE: 1

Glu Ile His Gly Ser Leu Phe Lys
1               5

<210> SEQ ID NO 2
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (6)..(6)
<223> OTHER INFORMATION: AMIDATION

<400> SEQUENCE: 2

His Gly Ser Leu Phe Lys
1               5

<210> SEQ ID NO 3
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (8)..(8)
<223> OTHER INFORMATION: AMIDATION
```

```
<400> SEQUENCE: 3

Leu Val Gly Ala Gly Val Ser Ala
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic peptide

<400> SEQUENCE: 4

Gly Ala Gly Val Ser Ala Glu
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (7)..(7)
<223> OTHER INFORMATION: AMIDATION

<400> SEQUENCE: 5

Gly Ala Gly Val Ser Ala Glu
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic peptide

<400> SEQUENCE: 6

Thr Gln Asn Ile Asp Glu Leu
1               5

<210> SEQ ID NO 7
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (7)..(7)
<223> OTHER INFORMATION: AMIDATION

<400> SEQUENCE: 7

Thr Gln Asn Ile Asp Glu Leu
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (8)..(8)
<223> OTHER INFORMATION: AMIDATION

<400> SEQUENCE: 8

Val Ile Thr Gln Asn Ile Asp Ala
```

<210> SEQ ID NO 9
<211> LENGTH: 747
<212> TYPE: PRT
<213> ORGANISM: Artificial Sequence
<220> FEATURE:
<223> OTHER INFORMATION: hSIRT1

<400> SEQUENCE: 9

```
Met Ala Asp Glu Ala Ala Leu Ala Leu Gln Pro Gly Gly Ser Pro Ser
1               5                   10                  15

Ala Ala Gly Ala Asp Arg Glu Ala Ala Ser Pro Ala Gly Glu Pro
            20                  25                  30

Leu Arg Lys Arg Pro Arg Arg Asp Gly Pro Gly Leu Glu Arg Ser Pro
            35                  40                  45

Gly Glu Pro Gly Gly Ala Ala Pro Glu Arg Glu Val Pro Ala Ala Ala
        50                  55                  60

Arg Gly Cys Pro Gly Ala Ala Ala Ala Leu Trp Arg Glu Ala Glu
65                  70                  75                  80

Ala Glu Ala Ala Ala Gly Gly Glu Gln Glu Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
        355                 360                 365
```

```
Ala Ser Cys Leu Ile Cys Lys Tyr Lys Val Asp Cys Glu Ala Val Arg
    370                 375                 380
Gly Asp Ile Phe Asn Gln Val Val Pro Arg Cys Pro Arg Cys Pro Ala
385                 390                 395                 400
Asp Glu Pro Leu Ala Ile Met Lys Pro Glu Ile Val Phe Phe Gly Glu
                405                 410                 415
Asn Leu Pro Glu Gln Phe His Arg Ala Met Lys Tyr Asp Lys Asp Glu
            420                 425                 430
Val Asp Leu Leu Ile Val Ile Gly Ser Ser Leu Lys Val Arg Pro Val
        435                 440                 445
Ala Leu Ile Pro Ser Ser Ile Pro His Glu Val Pro Gln Ile Leu Ile
    450                 455                 460
Asn Arg Glu Pro Leu Pro His Leu His Phe Asp Val Glu Leu Leu Gly
465                 470                 475                 480
Asp Cys Asp Val Ile Ile Asn Glu Leu Cys His Arg Leu Gly Gly Glu
                485                 490                 495
Tyr Ala Lys Leu Cys Cys Asn Pro Val Lys Leu Ser Glu Ile Thr Glu
            500                 505                 510
Lys Pro Pro Arg Thr Gln Lys Glu Leu Ala Tyr Leu Ser Glu Leu Pro
        515                 520                 525
Pro Thr Pro Leu His Val Ser Glu Asp Ser Ser Ser Pro Glu Arg Thr
    530                 535                 540
Ser Pro Pro Asp Ser Ser Val Ile Val Thr Leu Leu Asp Gln Ala Ala
545                 550                 555                 560
Lys Ser Asn Asp Asp Leu Asp Val Ser Glu Ser Lys Gly Cys Met Glu
                565                 570                 575
Glu Lys Pro Gln Glu Val Gln Thr Ser Arg Asn Val Glu Ser Ile Ala
            580                 585                 590
Glu Gln Met Glu Asn Pro Asp Leu Lys Asn Val Gly Ser Ser Thr Gly
        595                 600                 605
Glu Lys Asn Glu Arg Thr Ser Val Ala Gly Thr Val Arg Lys Cys Trp
    610                 615                 620
Pro Asn Arg Val Ala Lys Glu Gln Ile Ser Arg Arg Leu Asp Gly Asn
625                 630                 635                 640
Gln Tyr Leu Phe Leu Pro Pro Asn Arg Tyr Ile Phe His Gly Ala Glu
                645                 650                 655
Val Tyr Ser Asp Ser Glu Asp Asp Val Leu Ser Ser Ser Ser Cys Gly
            660                 665                 670
Ser Asn Ser Asp Ser Gly Thr Cys Gln Ser Pro Ser Leu Glu Glu Pro
        675                 680                 685
Met Glu Asp Glu Ser Glu Ile Glu Glu Phe Tyr Asn Gly Leu Glu Asp
    690                 695                 700
Glu Pro Asp Val Pro Glu Arg Ala Gly Gly Ala Gly Phe Gly Thr Asp
705                 710                 715                 720
Gly Asp Asp Gln Glu Ala Ile Asn Glu Ala Ile Ser Val Lys Gln Glu
                725                 730                 735
Val Thr Asp Met Asn Tyr Pro Ser Asn Lys Ser
            740                 745

<210> SEQ ID NO 10
<211> LENGTH: 389
<212> TYPE: PRT
<213> ORGANISM: Artificial Sequence
<220> FEATURE:
<223> OTHER INFORMATION: hSIRT2
```

<400> SEQUENCE: 10

```
Met Ala Glu Pro Asp Pro Ser His Pro Leu Glu Thr Gln Ala Gly Lys
1               5                   10                  15

Val Gln Glu Ala Gln Asp Ser Asp Ser Asp Ser Glu Gly Gly Ala Ala
            20                  25                  30

Gly Gly Glu Ala Asp Met Asp Phe Leu Arg Asn Leu Phe Ser Gln Thr
        35                  40                  45

Leu Ser Leu Gly Ser Gln Lys Glu Arg Leu Leu Asp Glu Leu Thr Leu
    50                  55                  60

Glu Gly Val Ala Arg Tyr Met Gln Ser Glu Arg Cys Arg Arg Val Ile
65                  70                  75                  80

Cys Leu Val Gly Ala Gly Ile Ser Thr Ser Ala Gly Ile Pro Asp Phe
                85                  90                  95

Arg Ser Pro Ser Thr Gly Leu Tyr Asp Asn Leu Glu Lys Tyr His Leu
            100                 105                 110

Pro Tyr Pro Glu Ala Ile Phe Glu Ile Ser Tyr Phe Lys Lys His Pro
        115                 120                 125

Glu Pro Phe Phe Ala Leu Ala Lys Glu Leu Tyr Pro Gly Gln Phe Lys
    130                 135                 140

Pro Thr Ile Cys His Tyr Phe Met Arg Leu Leu Lys Asp Lys Gly Leu
145                 150                 155                 160

Leu Leu Arg Cys Tyr Thr Gln Asn Ile Asp Thr Leu Glu Arg Ile Ala
                165                 170                 175

Gly Leu Glu Gln Glu Asp Leu Val Glu Ala His Gly Thr Phe Tyr Thr
            180                 185                 190

Ser His Cys Val Ser Ala Ser Cys Arg His Glu Tyr Pro Leu Ser Trp
        195                 200                 205

Met Lys Glu Lys Ile Phe Ser Glu Val Thr Pro Lys Cys Glu Asp Cys
    210                 215                 220

Gln Ser Leu Val Lys Pro Asp Ile Val Phe Phe Gly Glu Ser Leu Pro
225                 230                 235                 240

Ala Arg Phe Phe Ser Cys Met Gln Ser Asp Phe Leu Lys Val Asp Leu
                245                 250                 255

Leu Leu Val Met Gly Thr Ser Leu Gln Val Gln Pro Phe Ala Ser Leu
            260                 265                 270

Ile Ser Lys Ala Pro Leu Ser Thr Pro Arg Leu Leu Ile Asn Lys Glu
        275                 280                 285

Lys Ala Gly Gln Ser Asp Pro Phe Leu Gly Met Ile Met Gly Leu Gly
    290                 295                 300

Gly Gly Met Asp Phe Asp Ser Lys Lys Ala Tyr Arg Asp Val Ala Trp
305                 310                 315                 320

Leu Gly Glu Cys Asp Gln Gly Cys Leu Ala Leu Ala Glu Leu Leu Gly
                325                 330                 335

Trp Lys Lys Glu Leu Glu Asp Leu Val Arg Arg Glu His Ala Ser Ile
            340                 345                 350

Asp Ala Gln Ser Gly Ala Gly Val Pro Asn Pro Ser Thr Ser Ala Ser
        355                 360                 365

Pro Lys Lys Ser Pro Pro Ala Lys Asp Glu Ala Arg Thr Thr Glu
    370                 375                 380

Arg Glu Lys Pro Gln
385
```

<210> SEQ ID NO 11

-continued

```
<211> LENGTH: 399
<212> TYPE: PRT
<213> ORGANISM: Artificial Sequence
<220> FEATURE:
<223> OTHER INFORMATION: hSIRT3

<400> SEQUENCE: 11

Met Ala Phe Trp Gly Trp Arg Ala Ala Ala Leu Arg Leu Trp Gly
  1               5                  10                  15

Arg Val Val Glu Arg Val Glu Ala Gly Gly Val Gly Pro Phe Gln
             20                  25                  30

Ala Cys Gly Cys Arg Leu Val Leu Gly Gly Arg Asp Asp Val Ser Ala
         35                  40                  45

Gly Leu Arg Gly Ser His Gly Ala Arg Gly Glu Pro Leu Asp Pro Ala
     50                  55                  60

Arg Pro Leu Gln Arg Pro Pro Arg Pro Glu Val Pro Arg Ala Phe Arg
 65                  70                  75                  80

Arg Gln Pro Arg Ala Ala Ala Pro Ser Phe Phe Phe Ser Ser Ile Lys
                 85                  90                  95

Gly Gly Arg Arg Ser Ile Ser Phe Ser Val Gly Ala Ser Ser Val Val
            100                 105                 110

Gly Ser Gly Gly Ser Ser Asp Lys Gly Lys Leu Ser Leu Gln Asp Val
        115                 120                 125

Ala Glu Leu Ile Arg Ala Arg Ala Cys Gln Arg Val Val Met Val
    130                 135                 140

Gly Ala Gly Ile Ser Thr Pro Ser Gly Ile Pro Asp Phe Arg Ser Pro
145                 150                 155                 160

Gly Ser Gly Leu Tyr Ser Asn Leu Gln Gln Tyr Asp Leu Pro Tyr Pro
                165                 170                 175

Glu Ala Ile Phe Glu Leu Pro Phe Phe Phe His Asn Pro Lys Pro Phe
            180                 185                 190

Phe Thr Leu Ala Lys Glu Leu Tyr Pro Gly Asn Tyr Lys Pro Asn Val
        195                 200                 205

Thr His Tyr Phe Leu Arg Leu Leu His Asp Lys Gly Leu Leu Leu Arg
    210                 215                 220

Leu Tyr Thr Gln Asn Ile Asp Gly Leu Glu Arg Val Ser Gly Ile Pro
225                 230                 235                 240

Ala Ser Lys Leu Val Glu Ala His Gly Thr Phe Ala Ser Ala Thr Cys
                245                 250                 255

Thr Val Cys Gln Arg Pro Phe Pro Gly Glu Asp Ile Arg Ala Asp Val
            260                 265                 270

Met Ala Asp Arg Val Pro Arg Cys Pro Val Cys Thr Gly Val Val Lys
        275                 280                 285

Pro Asp Ile Val Phe Phe Gly Glu Pro Leu Pro Gln Arg Phe Leu Leu
    290                 295                 300

His Val Val Asp Phe Pro Met Ala Asp Leu Leu Leu Ile Leu Gly Thr
305                 310                 315                 320

Ser Leu Glu Val Glu Pro Phe Ala Ser Leu Thr Glu Ala Val Arg Ser
                325                 330                 335

Ser Val Pro Arg Leu Leu Ile Asn Arg Asp Leu Val Gly Pro Leu Ala
            340                 345                 350

Trp His Pro Arg Ser Arg Asp Val Ala Gln Leu Gly Asp Val Val His
        355                 360                 365

Gly Val Glu Ser Leu Val Glu Leu Leu Gly Trp Thr Glu Glu Met Arg
    370                 375                 380
```

```
Asp Leu Val Gln Arg Glu Thr Gly Lys Leu Asp Gly Pro Asp Lys
385                 390                 395

<210> SEQ ID NO 12
<211> LENGTH: 314
<212> TYPE: PRT
<213> ORGANISM: Artificial Sequence
<220> FEATURE:
<223> OTHER INFORMATION: hSIRT4

<400> SEQUENCE: 12

Met Lys Met Ser Phe Ala Leu Thr Phe Arg Ser Ala Lys Gly Arg Trp
1               5                   10                  15

Ile Ala Asn Pro Ser Gln Pro Cys Ser Lys Ala Ser Ile Gly Leu Phe
            20                  25                  30

Val Pro Ala Ser Pro Leu Asp Pro Glu Lys Val Lys Glu Leu Gln
        35                  40                  45

Arg Phe Ile Thr Leu Ser Lys Arg Leu Leu Val Met Thr Gly Ala Gly
    50                  55                  60

Ile Ser Thr Glu Ser Gly Ile Pro Asp Tyr Arg Ser Glu Lys Val Gly
65                  70                  75                  80

Leu Tyr Ala Arg Thr Asp Arg Arg Pro Ile Gln His Gly Asp Phe Val
                85                  90                  95

Arg Ser Ala Pro Ile Arg Gln Arg Tyr Trp Ala Arg Asn Phe Val Gly
            100                 105                 110

Trp Pro Gln Phe Ser Ser His Gln Pro Asn Pro Ala His Trp Ala Leu
        115                 120                 125

Ser Thr Trp Glu Lys Leu Gly Lys Leu Tyr Trp Leu Val Thr Gln Asn
    130                 135                 140

Val Asp Ala Leu His Thr Lys Ala Gly Ser Arg Arg Leu Thr Glu Leu
145                 150                 155                 160

His Gly Cys Met Asp Arg Val Leu Cys Leu Asp Cys Gly Glu Gln Thr
                165                 170                 175

Pro Arg Gly Val Leu Gln Glu Arg Phe Gln Val Leu Asn Pro Thr Trp
            180                 185                 190

Ser Ala Glu Ala His Gly Leu Ala Pro Asp Gly Asp Val Phe Leu Ser
        195                 200                 205

Glu Glu Gln Val Arg Ser Phe Gln Val Pro Thr Cys Val Gln Cys Gly
    210                 215                 220

Gly His Leu Lys Pro Asp Val Val Phe Phe Gly Asp Thr Val Asn Pro
225                 230                 235                 240

Asp Lys Val Asp Phe Val His Lys Arg Val Lys Glu Ala Asp Ser Leu
                245                 250                 255

Leu Val Val Gly Ser Ser Leu Gln Val Tyr Ser Gly Tyr Arg Phe Ile
            260                 265                 270

Leu Thr Ala Trp Glu Lys Lys Leu Pro Ile Ala Ile Leu Asn Ile Gly
        275                 280                 285

Pro Thr Arg Ser Asp Asp Leu Ala Cys Leu Lys Leu Asn Ser Arg Cys
    290                 295                 300

Gly Glu Leu Leu Pro Leu Ile Asp Pro Cys
305                 310

<210> SEQ ID NO 13
<211> LENGTH: 310
<212> TYPE: PRT
<213> ORGANISM: Artificial Sequence
<220> FEATURE:
<223> OTHER INFORMATION: hSIRT5
```

<400> SEQUENCE: 13

Met Arg Pro Leu Gln Ile Val Pro Ser Arg Leu Ile Ser Gln Leu Tyr
1               5                   10                  15

Cys Gly Leu Lys Pro Pro Ala Ser Thr Arg Asn Gln Ile Cys Leu Lys
            20                  25                  30

Met Ala Arg Pro Ser Ser Met Ala Asp Phe Arg Lys Phe Phe Ala
        35                  40                  45

Lys Ala Lys His Ile Val Ile Ile Ser Gly Ala Gly Val Ser Ala Glu
50                  55                  60

Ser Gly Val Pro Thr Phe Arg Gly Ala Gly Gly Tyr Trp Arg Lys Trp
65                  70                  75                  80

Gln Ala Gln Asp Leu Ala Thr Pro Leu Ala Phe Ala His Asn Pro Ser
                85                  90                  95

Arg Val Trp Glu Phe Tyr His Tyr Arg Arg Glu Val Met Gly Ser Lys
            100                 105                 110

Glu Pro Asn Ala Gly His Arg Ala Ile Ala Glu Cys Glu Thr Arg Leu
        115                 120                 125

Gly Lys Gln Gly Arg Arg Val Val Val Ile Thr Gln Asn Ile Asp Glu
130                 135                 140

Leu His Arg Lys Ala Gly Thr Lys Asn Leu Leu Glu Ile His Gly Ser
145                 150                 155                 160

Leu Phe Lys Thr Arg Cys Thr Ser Cys Gly Val Val Ala Glu Asn Tyr
                165                 170                 175

Lys Ser Pro Ile Cys Pro Ala Leu Ser Gly Lys Gly Ala Pro Glu Pro
            180                 185                 190

Gly Thr Gln Asp Ala Ser Ile Pro Val Glu Lys Leu Pro Arg Cys Glu
        195                 200                 205

Glu Ala Gly Cys Gly Gly Leu Leu Arg Pro His Val Val Trp Phe Gly
210                 215                 220

Glu Asn Leu Asp Pro Ala Ile Leu Glu Glu Val Asp Arg Glu Leu Ala
225                 230                 235                 240

His Cys Asp Leu Cys Leu Val Val Gly Thr Ser Ser Val Val Tyr Pro
                245                 250                 255

Ala Ala Met Phe Ala Pro Gln Val Ala Ala Arg Gly Val Pro Val Ala
            260                 265                 270

Glu Phe Asn Thr Glu Thr Thr Pro Ala Thr Asn Arg Phe Arg Phe His
        275                 280                 285

Phe Gln Gly Pro Cys Gly Thr Thr Leu Pro Glu Ala Leu Ala Cys His
290                 295                 300

Glu Asn Glu Thr Val Ser
305                 310

<210> SEQ ID NO 14
<211> LENGTH: 355
<212> TYPE: PRT
<213> ORGANISM: Artificial Sequence
<220> FEATURE:
<223> OTHER INFORMATION: hSIRT6

<400> SEQUENCE: 14

Met Ser Val Asn Tyr Ala Ala Gly Leu Ser Pro Tyr Ala Asp Lys Gly
1               5                   10                  15

Lys Cys Gly Leu Pro Glu Ile Phe Asp Pro Pro Glu Glu Leu Glu Arg
            20                  25                  30

Lys Val Trp Glu Leu Ala Arg Leu Val Trp Gln Ser Ser Ser Val Val

```
                35                  40                  45
Phe His Thr Gly Ala Gly Ile Ser Thr Ala Ser Gly Ile Pro Asp Phe
 50                  55                  60

Arg Gly Pro His Gly Val Trp Thr Met Glu Glu Arg Gly Leu Ala Pro
 65                  70                  75                  80

Lys Phe Asp Thr Thr Phe Glu Ser Ala Arg Pro Thr Gln Thr His Met
                 85                  90                  95

Ala Leu Val Gln Leu Glu Arg Val Gly Leu Leu Arg Phe Leu Val Ser
                100                 105                 110

Gln Asn Val Asp Gly Leu His Val Arg Ser Gly Phe Pro Arg Asp Lys
            115                 120                 125

Leu Ala Glu Leu His Gly Asn Met Phe Val Glu Glu Cys Ala Lys Cys
130                 135                 140

Lys Thr Gln Tyr Val Arg Asp Thr Val Val Gly Thr Met Gly Leu Lys
145                 150                 155                 160

Ala Thr Gly Arg Leu Cys Thr Val Ala Lys Ala Arg Gly Leu Arg Ala
                165                 170                 175

Cys Arg Gly Glu Leu Arg Asp Thr Ile Leu Asp Trp Glu Asp Ser Leu
            180                 185                 190

Pro Asp Arg Asp Leu Ala Leu Ala Asp Glu Ala Ser Arg Asn Ala Asp
        195                 200                 205

Leu Ser Ile Thr Leu Gly Thr Ser Leu Gln Ile Arg Pro Ser Gly Asn
210                 215                 220

Leu Pro Leu Ala Thr Lys Arg Arg Gly Gly Arg Leu Val Ile Val Asn
225                 230                 235                 240

Leu Gln Pro Thr Lys His Asp Arg His Ala Asp Leu Arg Ile His Gly
                245                 250                 255

Tyr Val Asp Glu Val Met Thr Arg Leu Met Glu His Leu Gly Leu Glu
            260                 265                 270

Ile Pro Ala Trp Asp Gly Pro Arg Val Leu Glu Arg Ala Leu Pro Pro
        275                 280                 285

Leu Pro Arg Pro Pro Thr Pro Lys Leu Glu Pro Lys Glu Glu Ser Pro
290                 295                 300

Thr Arg Ile Asn Gly Ser Ile Pro Ala Gly Pro Lys Gln Glu Pro Cys
305                 310                 315                 320

Ala Gln His Asn Gly Ser Glu Pro Ala Ser Pro Lys Arg Glu Arg Pro
                325                 330                 335

Thr Ser Pro Ala Pro His Arg Pro Pro Lys Arg Val Lys Ala Lys Ala
            340                 345                 350

Val Pro Ser
        355

<210> SEQ ID NO 15
<211> LENGTH: 400
<212> TYPE: PRT
<213> ORGANISM: Artificial Sequence
<220> FEATURE:
<223> OTHER INFORMATION: hSIRT7

<400> SEQUENCE: 15

Met Ala Ala Gly Gly Leu Ser Arg Ser Glu Arg Lys Ala Ala Glu Arg
  1               5                  10                  15

Val Arg Arg Leu Arg Glu Glu Gln Gln Arg Glu Arg Leu Arg Gln Val
                 20                  25                  30

Ser Arg Ile Leu Arg Lys Ala Ala Ala Glu Arg Ser Ala Glu Glu Gly
                 35                  40                  45
```

```
Arg Leu Leu Ala Glu Ser Ala Asp Leu Val Thr Glu Leu Gln Gly Arg
    50                  55                  60

Ser Arg Arg Arg Glu Gly Leu Lys Arg Gln Glu Glu Val Cys Asp
65                  70                  75                  80

Asp Pro Glu Glu Leu Arg Gly Lys Val Arg Glu Leu Ala Ser Ala Val
                85                  90                  95

Arg Asn Ala Lys Tyr Leu Val Val Tyr Thr Gly Ala Gly Ile Ser Thr
                100                 105                 110

Ala Ala Ser Ile Pro Asp Tyr Arg Gly Pro Asn Gly Val Trp Thr Leu
            115                 120                 125

Leu Gln Lys Gly Arg Ser Val Ser Ala Ala Asp Leu Ser Glu Ala Glu
    130                 135                 140

Pro Thr Leu Thr His Met Ser Ile Thr Arg Leu His Glu Gln Lys Leu
145                 150                 155                 160

Val Gln His Val Val Ser Gln Asn Cys Asp Gly Leu His Leu Arg Ser
                165                 170                 175

Gly Leu Pro Arg Thr Ala Ile Ser Glu Leu His Gly Asn Met Tyr Ile
            180                 185                 190

Glu Val Cys Thr Ser Cys Val Pro Asn Arg Glu Tyr Val Arg Val Phe
        195                 200                 205

Asp Val Thr Glu Arg Thr Ala Leu His Arg His Gln Thr Gly Arg Thr
    210                 215                 220

Cys His Lys Cys Gly Thr Gln Leu Arg Asp Thr Ile Val His Phe Gly
225                 230                 235                 240

Glu Arg Gly Thr Leu Gly Gln Pro Leu Asn Trp Glu Ala Ala Thr Glu
            245                 250                 255

Ala Ala Ser Arg Ala Asp Thr Ile Leu Cys Leu Gly Ser Ser Leu Lys
            260                 265                 270

Val Leu Lys Lys Tyr Pro Arg Leu Trp Cys Met Thr Lys Pro Pro Ser
        275                 280                 285

Arg Arg Pro Lys Leu Tyr Ile Val Asn Leu Gln Trp Thr Pro Lys Asp
    290                 295                 300

Asp Trp Ala Ala Leu Lys Leu His Gly Lys Cys Asp Asp Val Met Arg
305                 310                 315                 320

Leu Leu Met Ala Glu Leu Gly Leu Glu Ile Pro Ala Tyr Ser Arg Trp
            325                 330                 335

Gln Asp Pro Ile Phe Ser Leu Ala Thr Pro Leu Arg Ala Gly Glu Glu
        340                 345                 350

Gly Ser His Ser Arg Lys Ser Leu Cys Arg Ser Arg Glu Glu Ala Pro
        355                 360                 365

Pro Gly Asp Arg Gly Ala Pro Leu Ser Ser Ala Pro Ile Leu Gly Gly
    370                 375                 380

Trp Phe Gly Arg Gly Cys Thr Lys Arg Thr Lys Arg Lys Lys Val Thr
385                 390                 395                 400
```